(12) United States Patent
Levine et al.

(10) Patent No.: US 7,914,828 B2
(45) Date of Patent: Mar. 29, 2011

(54) COMBINATION HERBAL PRODUCT TO BENEFIT RESPIRATORY TRACT

(76) Inventors: Brian M. Levine, Coto de Caza, CA (US); William Berger, Coto de Caza, CA (US)

( * ) Notice: Subject to any disclaimer, the term of this patent is extended or adjusted under 35 U.S.C. 154(b) by 0 days.

(21) Appl. No.: 12/581,617

(22) Filed: Oct. 19, 2009

(65) Prior Publication Data
US 2010/0098790 A1    Apr. 22, 2010

Related U.S. Application Data

(60) Provisional application No. 61/106,250, filed on Oct. 17, 2008.

(51) Int. Cl.
*A61K 36/53* (2006.01)

(52) U.S. Cl. ........ 424/725; 424/735; 424/766; 424/774; 424/775; 424/776

(58) Field of Classification Search .................. None
See application file for complete search history.

(56) References Cited

U.S. PATENT DOCUMENTS

| | | | |
|---|---|---|---|
| 3,061,517 A | 10/1962 | Lewis et al. | |
| 4,619,934 A | 10/1986 | Sunshine et al. | |
| 4,840,949 A | 6/1989 | Korbonits et al. | |
| 5,681,577 A | 10/1997 | Leech et al. | |
| 6,037,358 A | 3/2000 | Gordziel | |
| 6,306,904 B1 | 10/2001 | Gordziel | |
| 6,319,513 B1 | 11/2001 | Dobrozsi et al. | |
| 6,348,470 B1 | 2/2002 | Korbonits et al. | |
| 6,362,197 B1 | 3/2002 | Page et al. | |
| 6,417,206 B1 | 7/2002 | Leflein et al. | |
| 6,509,492 B1 | 1/2003 | Venkataraman et al. | |
| 6,638,521 B2 | 10/2003 | Dobrozsi et al. | |
| 6,670,370 B1 | 12/2003 | Chopdekar et al. | |
| 6,790,980 B1 | 9/2004 | Venkataraman et al. | |
| 6,979,689 B2 | 12/2005 | Gonzales et al. | |
| 2002/0009478 A1 | 1/2002 | Dobrozsi et al. | |
| 2002/0082307 A1 | 6/2002 | Dobrozsi et al. | |
| 2003/0077321 A1 | 4/2003 | Kiel et al. | |
| 2003/0118613 A1 | 6/2003 | Dobrozsi et al. | |
| 2004/0029864 A1 | 2/2004 | MacMillan | |
| 2004/0033961 A1 | 2/2004 | Gremminger et al. | |
| 2005/0020509 A1 | 1/2005 | Kiel et al. | |

*Primary Examiner* — Susan C Hoffman

(74) *Attorney, Agent, or Firm* — Stetina Brunda Garred & Brucker

(57) ABSTRACT

An herbal composition for providing a beneficial effect to the respiratory tract. The composition includes Colt's Foot, Mangosteen, Thyme Leaf, Wild Cherry Bark, Quercitin, Sundew, Butterbur, and Grape Seed Extract. In particular, the composition may prevent or treat cough. Also described are methods of using the herbal composition.

7 Claims, 1 Drawing Sheet

| FREQUENCY OF COUGH EPISODES | Visit 1 | Visit 2 | Visit 3 | Visit 4 | Visit 5 |
|---|---|---|---|---|---|
| None | | | | | |
| Almost Never: 0-2 spells per day | | | | | |
| Little: 3-14 spells per day | | | | | |
| Somewhat: 15-30 spells per day | | | | | |
| Much: 31-40 spells per day | | | | | |
| Very Much: 40+ spells per day | | | | | |

| SEVERITY OF COUGH EPISODES | Visit 1 | Visit 2 | Visit 3 | Visit 4 | Visit 5 |
|---|---|---|---|---|---|
| Mild | | | | | |
| Moderate | | | | | |
| Severe | | | | | |
| Very Severe | | | | | |

Figure 1

COMBINATION HERBAL PRODUCT TO BENEFIT RESPIRATORY TRACT

CROSS-REFERENCE TO RELATED APPLICATIONS

This application claims the benefit of U.S. Provisional Application No. 61/106,250, filed on Oct. 17, 2008, the teachings of which are expressly incorporated by reference.

STATEMENT RE: FEDERALLY SPONSORED RESEARCH/DEVELOPMENT

Not Applicable

BACKGROUND

1. Field of the Invention

The present invention relates to a novel synergistic herbal composition for providing beneficial effects to the respiratory tract of a mammal. In particular, the herbal composition may be used for preventing and treating cough. The herbs in the present invention include Colt's Foot, Mangosteen, Thyme Leaf, Wild Cherry Bark, Quercitin, Sundew, Butterbur, and Grape Seed Extract.

2. Background of the Invention

Disorders of the respiratory tract, such as nasal congestion, cough, wheezing, and breathing difficulties are common occurrences. For example, cough is the number one reason that patients seek medical attention, estimated to be over 30 million office visits per year in the United States alone. The act of coughing is a protective reflex. However, persistent cough is abnormal and is due to either a single medical cause (e.g., Upper Respiratory Infection [URI]) or multiple causes (e.g., chronic post nasal drainage, gastroesophageal reflux, asthma, etc.). Coughing can dramatically affect one's quality of life when it becomes excessive and/or profound. Also, the financial burden of people coughing can be staggering, due to the purchase of expensive medications, as well as need for multiple office visits and medical testing/procedures.

It has been demonstrated that over the counter cough suppressants and expectorants have proven to be ineffective. Furthermore, many of these medications have been demonstrated to cause adverse side effects, especially in children. The only prescription cough medicine proven to be beneficial, according to The American College of Chest Physicians, is codeine. However, it has been documented that prescribed codeine derivative products suppress cough only at doses that cause side effects, such as gastrointestinal constipation, sedation, and respiratory depression. It becomes apparent that there remain few, if any, pharmaceutical products, commercially available, that have been found to actually benefit the respiratory tract.

On the other hand, there has been a surge in those interested in the benefits of herbal medicine. Even though patients may welcome herbal treatments for cough enthusiastically, sound evidence for their efficacy has been lacking.

Herbal products, in the form of nutritional supplements, have been used for centuries to treat medical disorders. Since a void exists for therapeutic products that actually work to support the respiratory tract, the use of herbal alternatives has gained greater attention. Furthermore, recent data has suggested that combinations of herbal supplements, such as has been used in traditional Chinese medicine, can provide benefits to the respiratory tract. Allergic rhinitis and asthma, for example, have been shown to improve when herbal products are combined. However, there has, as yet, been no scientific examination of the effect of herbal ingredient combinations specifically for cough.

BRIEF SUMMARY

The present invention encompasses a synergistic herbal combination, potentially in the form of a tablet, and is comprised of eight key ingredients that together support respiratory health. The eight ingredients have been commercially available for health benefits over the past several years. However, they have never been used in combination. Each tablet contains the following ingredients: Colt's Foot (*Tussilago farfara*), Mangosteen (*Garcinia mangostana*), Thyme Leaf (*Thymus vulgaris*), Wild Cherry Bark (*Prunus serotina*), Quercitin, Sundew (*Drosera ramentacea*), Butterbur (*Petasites hybridus*), and Grape Seed Extract with 10% oligomeric proanthocyanidin (OPC). It is contemplated that one may use commercially available herbal products to produce the presently disclosed synergistic herbal combination product.

In particular, one specific embodiment envisions an herbal composition for providing a beneficial effect to the respiratory tract of a mammal, including humans. The herbal composition may include the following as an active ingredient: Colt's Foot, Mangosteen, Thyme Leaf, Wild Cherry Bark, Quercitin, Sundew, Butterbur, and Grape Seed Extract. The herbal composition may be used to prevent or treat cough. Notably this may be achieved by one or more of the following beneficial aspects of the composition: cough suppression, demulcent, anti-inflammatory effect, antispasmodic, anti histamine, antioxidant, expectorant action, and bronchospastic relief.

It is envisioned that the herbal composition of the present invention may be formulated and administered in various forms, including, but not limited to dietary supplements and tablets. In particular, the herbal composition may include varied and numerous inactive ingredients known within the art to improve the formulation, delivery, preservation, appearance, and administration of the active ingredient.

Although the herbal composition is contemplated to be used in varying amounts of each herb, one particular embodiment utilizes a weight ratio of Colt's Foot, Mangosteen, Thyme Leaf, Wild Cherry Bark, Quercitin, Sundew, Butterbur, and Grape Seed Extract at about 6:6:6:6:5:6:1:0.1. In particular, and for the average adult human, the herbal composition may be formulated in the following amounts: 150 mg Colt's Foot, 150 mg Mangosteen, 150 mg Thyme Leaf, 150 mg Wild Cherry Bark, 125 mg Quercitin, 150 mg Sundew, 25 mg Butterbur, and 2.5 mg Grape Seed Extract. Alternatively, the herbal composition could be formulated in the following amounts: 300 mg Colt's Foot, 300 mg Mangosteen, 300 mg Thyme Leaf, 300 mg Wild Cherry Bark, 250 mg Quercitin, 300 mg Sundew, 50 mg Butterbur, and 5 mg Grape Seed Extract. In these instances, a patient could take two doses of the former to achieve the same results as a single dose of the latter.

It is believed that a preferred embodiment of the present invention would be within the following ranges: 150-600 mg Colt's Foot, 150-600 mg Mangosteen, 150-600 mg Thyme Leaf, 150-600 mg Wild Cherry Bark, 125-500 mg Quercitin, 125-600 mg Sundew, 25-100 mg Butterbur, and 2.5-100 mg Grape Seed Extract.

The present invention further contemplates a method of treating cough in a mammal by administering an effective amount of the herbal composition described herein to a mammal in need thereof. In particular, an adult human could receive beneficial effects by being administered, in tablet form, the herbal composition of the present invention, twice or thrice daily.

BRIEF DESCRIPTION OF THE DRAWINGS

These and other features and advantages of the various embodiments disclosed herein will be better understood with respect to the following description and drawings, in which:

FIG. 1 shows a sample chart for objectively monitoring frequency and severity of cough episodes.

DETAILED DESCRIPTION

The detailed description set forth below is intended as a description of the presently preferred embodiment of the invention, and is not intended to represent the only form in which the present invention may be constructed or utilized. The description sets forth the functions and sequences of steps for constructing and operating the invention. It is to be understood, however, that the same or equivalent functions and sequences may be accomplished by different embodiments and that they are also intended to be encompassed within the scope of the invention.

One embodiment of the present invention encompasses a novel synergistic herbal composition that benefits the respiratory tract. In particular, the novel herbal composition of this embodiment is useful in preventing and/or treating cough.

The act of coughing is a complicated process. Disturbance of the respiratory tract and/or gastrointestinal tract can trigger neurohumoral consequences that, ultimately, may result in cough. The cough reflex is truly a protective mechanism. However, in altered disease states, the cough frequency and severity can be greatly heightened, and dramatically affect one's quality of life.

Many patients have chronic cough due to a combination of multiple causes (e.g., gastroesophageal reflux, asthma, rhinitis, etc.) Other patients with chronic cough have no determined etiology. Regardless of cause, prior treatment outcomes for a large number of patients having chronic cough remain dismal. There are several ways in which herbal ingredients may act to treat cough, e.g., 1) via central nervous system action; 2) via local anesthetic effect 3) as a demulcent (soothing effect); 4) as a surfactant; 5) as an expectorant; 6) as a mucolytic; 7) as a antispasmodic; 8) as an anti-inflammant; 9) as an antioxidant; 10) as an antihistamine; or 11) as a decongestant. It would, indeed, seem likely that combined effects provided by multiple herbal ingredients could have a greater chance of treatment success in a patient population in which no modality has previously worked.

There are many combination herbal cough preparations commercially available throughout the world. However, the novel herbal combination of the present invention represents the first time that a combination herbal cough product has undergone both subjective as well as objective outcome measurement, similar to a pharmaceutical product investigation.

Components of the Herbal Composition

The novel herbal composition of the present invention includes the following active ingredients: Colt's foot, Mangosteen, Sundew, Thyme Leaf, Wild Cherry Bark, Quercitin, Butterbur, and Grape Seed Extract. Each of the listed active ingredients will be discussed in greater detail below. Furthermore, along with the active ingredients, it is contemplated that additional inactive ingredients, such as but not limited to carriers, adjuvants, diluents, fillers, emulsifiers, preservatives, and flavoring agents, may be added to the composition to prepare the composition in a suitable form for administration to a patient, e.g., tablet form.

Colt's Foot (*Tussilago farfara*) is a leaf extract that has been widely used as a demulcent (soothing effect) and antitussive (cough suppression). It has also been reported to provide symptomatic relief of asthma.

Mangosteen (*Garcinia mangostana*) is a fruit extract, which contains beneficial xanthones. It can provide antioxidant effect and can inhibit histamine release. Animal studies have suggested that Mangosteen inhibits cyclooxygenase (COX) and PGE 2 synthesis, thereby suppressing cough.

Thyme (*Thymus vulgaris*) is a leaf extract that contains volatile oils, such as thymol, as well as flavonoids (plant pigments). As a result, thyme commonly is used as an antitussive and antispasmodic. It also contains terpines that stimulate the cilia (fine hair-like structures in the lower respiratory tract) to beat and increase mucous movement to the upper respiratory tract (expectorant action). Furthermore, it has an anti-inflammatory effect, resulting in decreased nitric oxide production.

Wild Cherry Bark (*Prunus serotina*) is a tree bark extract that contains prunasin, a potent cough suppressant. It has also been reported to have an antioxidant effect. Wild Cherry Bark has, furthermore, been demonstrated to have a mild sedative effect, desirable during periods of illness.

Quercitin is a flavonoid (plant pigment). It both inhibits histamine release and decreases mast cell reactivity to histamine. It, also, blunts IgE mediated reactions. Quercitin has antioxidant activity by inhibiting cyclooxygenase (COX). It, furthermore, has been shown to decrease PGE2 production, thereby allowing for cough suppression.

Sundew (*Drosera ramentacea*) is a total plant extract that contains napthaquinones. The napthaquinones not only have an antispasmodic effect, but also have been found to have a profound antitussive effect equal to that of codeine.

Butterbur (*Petasites hybridus*) is a total plant extract that is anti-inflammatory (notably by the compounds petasin and/or isopetasin), in that it decreases histamine effect, as well as inhibiting leukotriene formation. It also has been widely used as a demulcent and anti-spasmodic.

Grape Seed Extract with 10% oligomeric proanthocyanidins (OPC) is a fruit seed extract containing polymers of flavonoids. It exerts remarkable anti-oxidant properties by scavenging free radicals.

All of the above listed compounds are known and available to those within the art. In the clinical trial below, the compounds were obtained from Blue California of Rancho Santa Margarita, Calif.

Example 1

Components and Effective Ranges

The components and effective dose ranges of the herbs used in herbal composition of the present invention are shown in Table 1.

TABLE 1

| Effective Dose Range | |
|---|---|
| Ingredient | Weight (mg) |
| Colt's Foot | 150-600 |
| Mangosteen | 150-600 |
| Thyme Leaf | 150-600 |

TABLE 1-continued

Effective Dose Range

| Ingredient | Weight (mg) |
| --- | --- |
| Wild Cherry Bark | 150-600 |
| Quercitin | 125-500 |
| Sundew | 150-600 |
| Butterbur | 25-100 |
| Grape Seed Extract | 2.5-100 |

Table 2 shows a first example of a tablet formulation of the present invention, wherein the tablet also contains the inactive ingredients cellulose, magnesium stearate, and silicon dioxide to prepare the tablet formulation.

TABLE 2

First Tablet Example

| Ingredient | Weight (mg) |
| --- | --- |
| Colt's Foot | 300 |
| Mangosteen | 300 |
| Thyme Leaf | 300 |
| Wild Cherry Bark | 300 |
| Quercitin | 250 |
| Sundew | 300 |
| Butterbur | 50 |
| Grape Seed Extract | 5 |

Table 3 shows a second example of a tablet formulation of the present invention. In particular, the formulation of Table 3 is the formulation used in the clinical study described below.

TABLE 3

Second Tablet Example

| Ingredient | Weight (mg) |
| --- | --- |
| Colt's Foot | 150 |
| Mangosteen | 150 |
| Thyme Leaf | 150 |
| Wild Cherry Bark | 150 |
| Quercitin | 125 |
| Sundew | 150 |
| Butterbur | 25 |
| Grape Seed Extract | 2.5 |

Suggested dosing for the described tablets to an average human patient would thus be 1-2 tablets, 2-3 times a day.

Example 2

Clinical Study

1. Patients

Eligible candidates were identified from a database of adult patients who had sought care at The Cough Center, in Laguna Hills, Calif. Traditionally, cough has been categorized in terms of duration, with acute cough defined as lasting less than 3 weeks, subacute cough lasting 3-8 weeks, and chronic cough lasting greater than 8 weeks. A total of 43 patients with chronic cough (39 women and 4 men) with a mean age of 55 years, were studied. The patients had previously undergone a complete evaluation and treatment program, following the guidelines established by The American College of Chest Physicians. All subjects shared a common history: 1) their cough persisted unabated for several years (chronic cough); 2) their cough profoundly diminished their quality of life; and 3) despite identification and treatment of causes by specialists, no medication(s) other than narcotic derivatives, were ever able to alleviate their cough. All patients were provided with written information prior to obtaining consent.

2. Study Design

The subjects participated in a three week study. Patients with severe and chronic cough, who had never been responsive to any medical treatment, except narcotic derivatives, were chosen. In this patient population, any improvement, even a small improvement can be viewed as being statistically significant. Because of the myriad of contributory causes resulting in chronic cough, randomized selections were impossible. Also, because the combination herbal product had such a unique taste, adequate placebo controls are difficult to devise. Regardless, it has been a well documented fact that placebo responses in chronic cough patients simply do not occur. This is possibly due to the prolonged duration of symptoms and multiple previous therapeutic trials. Therefore, patients with chronic cough serve as their own control.

Preceding the study, each patient underwent an initial office evaluation to rule out any recent or unrecognized cause of cough. All cough suppressants decongestants, antihistamines, anti-inflammatories, expectorants, and narcotics were eliminated prior to the study.

Each patient was required to take two tablets of the combination herbal product as described in Table 3, twice daily. At the end of the three week period of treatment, another office evaluation was performed. Subjective, as well as objective measurement techniques, then were administered at each office visit to determine success of treatment.

Each tablet contained Colts Foot (*Tussilago farfara*) 150 mg, Mangosteen (*Garcinia mangostana*) 150 mg., Thyme (*Thymus Vulgaris*) 150 mg., Wild Cherry Bark (*Prunus serotina*) 150 mg., Sundew (*Drosera ramentacea*) 150 mg, Butterbur (*Petasites hybridus*) 25 mg., Grape Seed Extract 2.5 mg, and Quercitin 125 mg.

3. Clinical Evaluation

The goal of successful treatment was cough resolution or cough reduced to the extent that it was no longer dominating one's quality of life (QOL). The assessment of treatment success was based on the positive trends noted with both subjective and objective evaluation. At pre- and post-treatment evaluations, a subjective measurement was attained using the Leicester Cough-Specific QOL Questionnaire. The questionnaire provides a validated and reproducible measure of the impact of chronic cough on activities of daily living. The subjects score the 19-item questionnaire based on physical, social, and psychological effects of cough. An objective system of cough monitoring was devised to assess both frequency and severity of coughing (FIG. 1). It should be noted that cough episodes or "epochs" were recorded rather than each individual cough. This system of evaluation became necessary because 1) a cough monitor for the many patients was impractical; 2) there is a wide difference of opinions as to what constitutes an individual "cough sound"; 3) the impact of coughing episodes seems to be recalled more accurately than each individual cough; and 4) the severity of coughing may have more of an impact than that of frequency of episodes. Each category of evaluation, frequency, severity, and Leicester QOL (LQOL) score was given equal weighting when treatment success was determined. For example, if frequency of episodes decreased 80-100%, severity diminished 75-100%, and LQOL score changed >2.6 points, then that individual would be categorized as being "improved". If frequency of episodes decreased 0-10%, severity diminished 0-15%, LQOL score changed <1.3 points, then that individual would be categorized as being "not improved". Individuals with values in between those two extremes were categorized as being "somewhat improved".

4. Statistical Analysis

Data for age and cough duration were expressed as median (range) values. Response rates were analyzed by paired ☐-tests. Group comparisons were performed using the Fisher two-tailed exact test. A value of $p<0.05$ was considered statistically significant.

5. Results

A total of 43 patients were initially enrolled in the study with a median (SD) age of 55 (10.2) years were studied. The median duration of cough was 6.5 years (78 months) with a range of 2 months to 60 years. Thirty-nine of the 43 patients were female. It is an established fact that female patients have an enhanced cough reflex sensitivity, compared to male patients, and represent the majority of patients seeking treatment for chronic cough.

Of the 43 patients, 3 had adverse side effects. Two patients had loose stools, and 1 patient had a diffuse skin rash. Two of the 3 patients stopped the herbal product, and dropped out of the study. The remaining 41 patients completed the three week study.

Upon evaluation, it was determined that 25 of the 41 patients studied (61%) demonstrated a statistically significant improvement in the frequency, severity, and subjective assessment of their quality of life, with the use of the combination herbal product. Of the 25 "improved" patients, 8 were "much improved" and 17 were "somewhat improved." Unfortunately, the cough for 16 patients was "not improved".

6. Conclusion

The results of this study showed that this particular novel combination herbal product can make a significant difference in the cough management in many patients with which no other treatment, short of (or including) narcotics, was successful. Furthermore, it has been demonstrated that the novel combination herbal product can be tolerated well, causing only minor side effects on an infrequent basis (<7%). Of greatest importance, however, is the fact that the novel combination herbal product has been shown to make a statistically significant improvement in the quality of life in patients having persistent cough.

The above description is given by way of example, and not limitation. Given the above disclosure, one skilled in the art could devise variations that are within the scope and spirit of the invention disclosed herein, including varying the amounts of each herbal composition and including additional inactive ingredients to make the composition more suitable for administration to a patient. Further, the various features of the embodiments disclosed herein can be used alone, or in varying combinations with each other and are not intended to be limited to the specific combination described herein. Thus, the scope of the claims is not to be limited by the illustrated embodiments.

What is claimed is:

1. A method of treating cough in a mammal, the method comprising administering an effective amount of an active ingredient consisting essentially of Colt's Foot, Mangosteen, Thyme Leaf, Wild Cherry Bark, Quercitin, Sundew, Butterbur, and Grape Seed Extract to a mammal in need thereof.

2. The method of claim 1, wherein the mammal is a human.

3. The method of claim 1, wherein the active ingredient consists essentially of 150-600 mg Colt's Foot, 150-600 mg Mangosteen, 150-600 mg Thyme Leaf, 150-600 mg Wild Cherry Bark, 125-500 mg Quercitin, 125-600 mg Sundew, 25-100 mg Butterbur, and 2.5-100 mg Grape Seed Extract.

4. The method of claim 3, wherein the active ingredient consists essentially of 300 mg Colt's Foot, 300 mg Mangosteen, 300 mg Thyme Leaf, 300 mg Wild Cherry Bark, 250 mg Quercitin, 300 mg Sundew, 50 mg Butterbur, and 5 mg Grape Seed Extract.

5. The method of claim 4, wherein the active ingredient is administered twice daily.

6. The method of claim 4, wherein the active ingredient is administered thrice daily.

7. The method of claim 1, wherein the active ingredient is administered to the mammal in tablet form.

* * * * *